(12) United States Patent
Peichel

(10) Patent No.: US 12,708,266 B2
(45) Date of Patent: Aug. 18, 2026

(54) ELECTRIC FIELD REJECTION OF A DUAL COIL TELEMETRY SYSTEM

(71) Applicant: Medtronic, Inc., Minneapolis, MN (US)

(72) Inventor: David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 908 days.

(21) Appl. No.: 18/146,216

(22) Filed: Dec. 23, 2022

(65) Prior Publication Data

US 2023/0240535 A1 Aug. 3, 2023

Related U.S. Application Data

(60) Provisional application No. 63/267,248, filed on Jan. 28, 2022.

(51) Int. Cl.

| | |
|---|---|
| ***A61B 5/00*** | (2006.01) |
| ***H01F 27/28*** | (2006.01) |
| ***H01F 27/30*** | (2006.01) |
| ***H01F 27/32*** | (2006.01) |

(52) U.S. Cl.

CPC ....... *A61B 5/0031* (2013.01); *H01F 27/2885* (2013.01); *H01F 27/303* (2013.01); *H01F 27/325* (2013.01)

(58) Field of Classification Search

CPC . A61B 5/0031; H01F 27/2885; H01F 27/303; H01F 27/325; H01F 2038/143; H01F 27/306; H01F 38/14; A61N 1/37223; A61N 1/37276

See application file for complete search history.

(56) References Cited

U.S. PATENT DOCUMENTS

| | | | |
|---|---|---|---|
| 5,324,315 A | 6/1994 | Grevious | |
| 6,201,993 B1 | 3/2001 | Kruse et al. | |
| 6,483,201 B1 * | 11/2002 | Klarer | B60K 28/14 307/10.6 |
| 8,285,396 B2 | 10/2012 | Bulkes et al. | |
| 8,548,597 B2 | 10/2013 | Dai et al. | |
| 2003/0052684 A1 * | 3/2003 | Nelson | G01V 3/105 324/329 |
| 2005/0033154 A1 | 2/2005 | deCharms | |

(Continued)

OTHER PUBLICATIONS

International Search Report and Written Opinion of International Application No. PCT/IB2023/050033 dated Apr. 4, 2023, 9 pp.

*Primary Examiner* — Amine Benlagsir

(74) *Attorney, Agent, or Firm* — Shumaker & Sieffert, P.A.

(57) ABSTRACT

An example telemetry system includes telemetry circuitry configured to communicate with a first device and being located on a circuit board. The telemetry system includes a first bobbin, the first bobbin being located on a first side of the circuit board. The telemetry system includes a first coil, the first coil being wound on the first bobbin in a first direction. The telemetry system includes a second bobbin, the second bobbin being located on a second side of the circuit board. The telemetry system includes a second coil, the second coil being wound on a second bobbin in a second direction, the second direction being opposite the first direction. An outer loop of the first coil and an outer loop of the second coil are electrically coupled together.

19 Claims, 7 Drawing Sheets

(56) References Cited

U.S. PATENT DOCUMENTS

| | | | | |
|---|---|---|---|---|
| 2005/0110700 | A1 | 5/2005 | Terry | |
| 2012/0063263 | A1* | 3/2012 | Kamata | G01V 1/182 367/182 |
| 2013/0194106 | A1* | 8/2013 | Lee | A61N 1/37223 340/870.3 |
| 2013/0310895 | A1 | 11/2013 | Pless et al. | |
| 2014/0275968 | A1 | 9/2014 | Stevenson et al. | |
| 2014/0293752 | A1* | 10/2014 | Fu | G01V 1/184 367/182 |
| 2016/0023007 | A1 | 1/2016 | Stouffer et al. | |
| 2019/0355510 | A1* | 11/2019 | Naor-Pomerantz | H01F 5/02 |
| 2020/0121936 | A1 | 4/2020 | Merlin | |
| 2020/0129773 | A1* | 4/2020 | Eisele | A61N 1/37252 |
| 2020/0306539 | A1 | 10/2020 | Kim et al. | |
| 2021/0364263 | A1* | 11/2021 | Knight | H02K 35/02 |

* cited by examiner

ELECTRIC FIELD REJECTION OF A DUAL COIL TELEMETRY SYSTEM

This application claims the benefit of U.S. Provisional Application No. 63/267,248, filed Jan. 28, 2022, the entirety of which is hereby incorporated by reference.

TECHNICAL FIELD

The disclosure relates to techniques for reducing electric field effects on a telemetry system.

BACKGROUND

A variety of implantable medical devices (IMDs) for delivering a therapy and/or monitoring a physiological condition have been clinically implanted or proposed for clinical implantation in patients. IMDs may deliver electrical or drug therapy and/or monitor conditions associated with the heart, muscle, nerve, brain, stomach or other organs or tissue.

IMDs, such as cardiac pacemakers or implantable cardioverter-defibrillators, for example, provide electrical therapy to the heart via electrodes carried by one or more implantable medical leads. The electrical therapy may include signals such as pacing pulses or shocks for cardioversion or defibrillation. In some cases, an IMD may sense intrinsic depolarizations of the heart, and control delivery of therapy signals to the heart based on the sensed depolarizations. Upon detection of an abnormal rhythm, such as bradycardia, tachycardia, or fibrillation, an appropriate electrical therapy signal or signals may be delivered to restore or maintain a more normal rhythm.

Such IMDs may also store and communicate sensed physiological parameters or other data to an external computing device via telemetry circuitry. In some examples, the external computing device may be used to program the IMD, such as to change a therapy regimen. The external computing device may include or be electrically coupled to a telemetry system which may receive data from the IMD and/or transmit data to the IMD.

SUMMARY

Telemetry systems which may be electrically coupled to or part of an external computing device may receive far field electric field noise which may interfere with communications between the external computing device and an implantable medical device (IMD). As used herein, far field electric field noise refers to electric field noise from a source that is relatively far away from the telemetry system when compared to the device with which the telemetry system is attempting to communicate. For example, if the received far field electric field noise is above a noise floor of the telemetry system, the integrity of the communication may be affected. As battery power of an IMD is limited, it may be desirable to reduce the number of times the IMD has to repeat the communication of the same data to the external medical device. As such, a telemetry system may be configured to reject or reduce the effect of far field electric field noise on the telemetry system.

This disclosure describes techniques for rejecting or reducing the effect of far field electric field noise on a telemetry system. For example, the telemetry system may include telemetry circuitry on a circuit board. The telemetry system may include a first bobbin located on a first side of the circuit board. The first bobbin may hold a first coil wound in a first direction. The telemetry system may also include a second bobbin located on a second side of the circuit board. The second bobbin may hold a second coil wound in a second direction that is opposite of the first directing. An outer loop of the first coil and an outer loop of the second coil may be electrically coupled together. In this manner, the telemetry system may reject or reduce the effect of far field electric field noise on the telemetry system as received far field noise on the first coil may be effectively canceled out by received far field noise on the second coil.

In some examples, rather than including a first bobbin located on a first side of the circuit board and a second bobbin located on a second side of the circuit board, the telemetry system may include at least one bobbin located on a first side of the circuit board. The at least one bobbin may hold the first coil wound in a first direction and a second coil wound in a second direction that is opposite of the first direction. An outer loop of the first coil and an outer loop of the second coil may be electrically coupled together.

In some examples, one portion of a switch may be coupled to the outer loop of the first coil and the outer loop of the second coil. The other side of the switch may be coupled to ground or earth (referred to hereinafter as ground). In such examples, the switch may be configured to be open when a receiver of the telemetry circuitry is not in use (e.g., not receiving data) and be closed when the receiver of the telemetry circuitry is in use (e.g., receiving data), thereby electrically coupling the outer loops to ground during use. In some examples, a surface of the first bobbin may be coated with a first conductive spray coating. In some examples, a surface of the second bobbin may be coated with a second conductive spray coating. In some examples, the first conductive spray coating may include a same material as the second conductive spray coating. In some examples, the first conductive spray coating may include a different material than the second conductive spray coating. In some examples, the conductive spray coatings may be coupled to ground. Each of these techniques may aid in the rejection or reduction of far field electric field noise.

In one aspect, this disclosure describes an example telemetry system comprising: telemetry circuitry configured to communicate with a first device and being located on a circuit board; a first bobbin, the first bobbin being located on a first side of the circuit board; a first coil, the first coil being wound on the first bobbin in a first direction; a second bobbin, the second bobbin being located on a second side of the circuit board; and a second coil, the second coil being wound on a second bobbin in a second direction, the second direction being opposite the first direction; wherein an outer loop of the first coil and an outer loop of the second coil are electrically coupled together.

In another aspect, this disclosure describes an example method comprising: placing telemetry circuitry on a circuit board, the telemetry circuitry being configured to communicate with a device; winding a first coil on a first bobbin in a first direction; winding a second coil on a second bobbin in a second direction, the second direction being opposite the first direction; placing the circuit board between the first bobbin and the second bobbin such that the first bobbin is located on a first side of the circuit board and the second bobbin is located on a second side of the circuit board; and electrically coupling an outer loop of the first coil to an outer loop of the second coil.

In another aspect, this disclosure describes an example telemetry system comprising: telemetry circuitry configured to communicate with a first device and being located on a circuit board; at least one bobbin, the at least one bobbin being located on a first side of the circuit board; a first coil, the first coil being wound on the at least one bobbin in a first direction; a second coil, the second coil being wound on the at least one bobbin in a second direction, the second direction being opposite the first direction; wherein an outer loop of the first coil and an outer loop of the second coil are electrically coupled together.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

As described above, methods, devices, and systems for rejecting or reducing the effect of far field electric field noise on a telemetry system are described in this disclosure. In the following description, references are made to illustrative examples. It is understood that other examples may be utilized without departing from the scope of the disclosure.

For coil coupled telemetry systems, a dual coil assembly with coils wound in opposite directions may be used to improve far field noise rejection while still permitting the sensing of near field magnetic or electric field sources. Traditionally, when exposed to electric field noise, the electric field can couple a voltage across the dual coils which may be electrically coupled in series which can then interfere with the intended receive signal. In some examples, such a telemetry system may include a programming head which may house telemetry circuitry used to communicate with an implantable medical device (IMB). In some cases, electric field shield covers, such as capacitive electric field shield covers, may be placed over the coils to help reject the electric field noise, but this may add cost and thickness to the programming head of the telemetry system. By electrically coupling the outer turns of the coils together, this may provide a first order rejection of the coupled far field electric field noise signal as the coupled far field electric field noise signal may be effectively shorted or canceled out. This may improve the electric field rejection of the programming head with the electric field shield covers, and may even eliminate the need for the electric field shield covers. In some examples, a conductive layer, such as a spray on conductive layer may be deposited on a surface of the bobbins for the coils, such as on an outer surface of the bobbins which may be connected to the circuit ground of the telemetry system, which may provide further rejection of electric field exposure on the faces of the coils, which would help alleviate the need for the electric field shield covers. Additionally, or alternatively, a switch electrically coupled to the outer loops of the two coils and ground may provide further rejection of electric field exposure on the faces of the coils.

Figure 1:
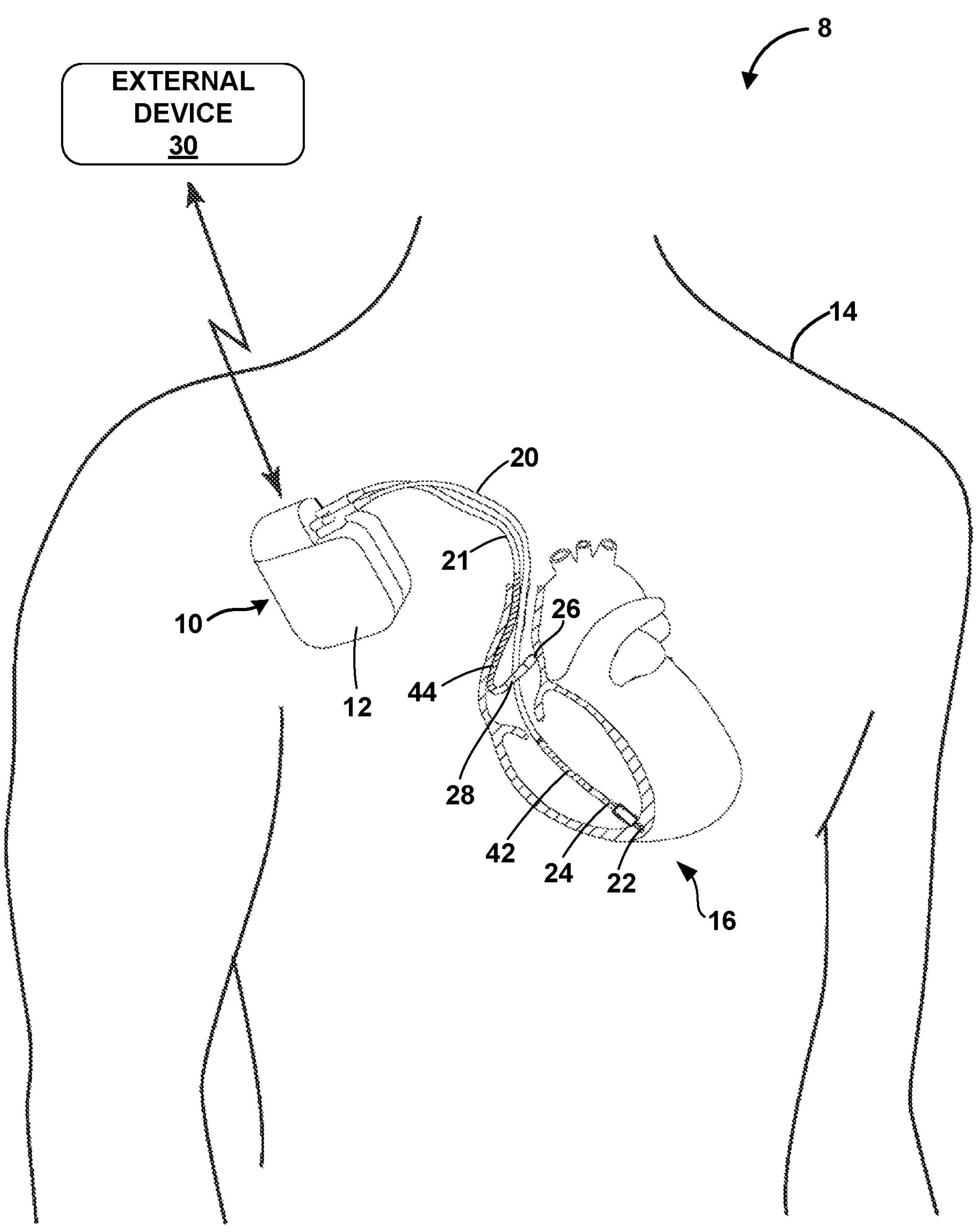
FIG. 1 is a conceptual diagram of an example implantable medical device system including an implantable medical device and an external device.

FIG. 1 is a conceptual diagram of an example implantable medical device system including an IMD and an external device. As illustrated in FIG. 1, a medical device system 8 for sensing cardiac events (e.g., P-waves and R-waves) and detecting tachyarrhythmia episodes, may include an IMD 10, a first (ventricular) implantable medical lead 20 and a second (atrial) implantable medical lead 21. In one example, IMD 10 may be an implantable cardioverter-defibrillator (ICD) capable of delivering pacing, cardioversion, and defibrillation therapy to the heart 16 of a patient 14. In other examples, IMD 10 may be a pacemaker capable of delivering pacing therapy, including anti-tachycardia pacing (ATP) to the patient, but need not include the capability of delivering cardioversion or defibrillation therapies. While primarily described herein as being techniques for rejecting or reducing far field noise when communicating with IMD 10, the techniques of this disclosure may be used for communication with any device, implantable or non-implantable, where such communication may be affected by far field electric field noise.

Ventricular lead 20 and atrial lead 21 are electrically coupled to IMD 10 and extend into heart 16. Ventricular lead 20 includes electrodes 22 and 24 shown positioned on the lead in the right ventricle (RV) of heart 16 for sensing ventricular electrogram (EGM) signals and pacing in the RV. Atrial lead 21 includes electrodes 26 and 28 positioned on the lead in the right atrium (RA) of heart 16 for sensing atrial EGM signals and pacing in the RA.

In the example of FIG. 1, ventricular lead 20 additionally carries a high voltage coil electrode 42, and atrial lead 21 carries a high voltage coil electrode 44, used to deliver cardioversion and defibrillation shock pulses. In other examples, ventricular lead 20 may carry both of high voltage coil electrodes 42 and 44, or may carry a high voltage coil electrode in addition to those illustrated in the example of FIG. 1. Both ventricular lead 20 and atrial lead 21 may be used to acquire cardiac EGM signals from patient 14 and to deliver therapy in response to the acquired data. Medical device system 8 is shown as a dual chamber ICD including atrial lead 21 and ventricular lead 20, but in some embodiments, system 8 may be a dual or multi-chamber system including a coronary sinus lead extending into the right atrium, through the coronary sinus and into a cardiac vein to position electrodes along the left ventricle (LV) for sensing LV EGM signals and delivering pacing pulses to the LV. In some examples, system 8 may be a single chamber system, or otherwise not include atrial lead 21.

IMD circuitry configured for performing the methods described herein and an associated battery or batteries are housed within a sealed housing 12 of IMD 10. Housing 12 may be conductive so as to serve as an electrode for use as an indifferent electrode during pacing or sensing or as an active electrode during defibrillation. As such, housing 12 is also referred to herein as “housing electrode” 12. In other examples, a different electrode may be separate from housing 12 and placed elsewhere on IMD 10, such as in the header. Implantable medical leads 20, 21 may include respective conductors connecting each of electrodes 22, 24, 26, 28, 42, and 44 to a connector assembly at the proximal end of the respective one of leads 20, 21, and thereby to the circuitry within housing 12 of IMD 10.

EGM signal data, cardiac rhythm episode data, and other data acquired by IMD 10 may be transmitted to an external device 30. External device 30 may be a computing device, e.g., used in a home, ambulatory, clinic, or hospital setting, to wirelessly communicate with IMD 10. External device 30 may be coupled to a remote patient monitoring system, such as Carelink®, available from Medtronic plc, of Dublin, Ireland. External device 30 may be, as examples, a programmer, external monitor, gateway, or consumer device (e.g., smart phone).

External device 30 may be used to program commands or operating parameters into IMD 10 for controlling IMD function, e.g., when configured as a programmer for IMD 10. External device 30 may be used to interrogate IMD 10 to retrieve data, including device operational data as well as physiological data accumulated in IMD memory. The interrogation may be automatic, e.g., according to a schedule, or in response to a remote or local user command. Programmers, external monitors, and consumer devices are examples of external devices 30 that may be used to interrogate IMD 10. Examples of communication techniques used by IMD 10 and external device 30 include radiofrequency (RF) telemetry, which may be an RF link established via Bluetooth, Wi-Fi, low frequency coupled coil (which may also be referred to as near field magnetic induction or NFMI), or medical implant communication service (MICS). Such communication techniques may be conducted by a telemetry system, which may be of external device 30 or may be coupled to external device 30.

Communication with IMD 10 may be relatively sensitive to noise, as the communication between IMD 10 and external device 30 must pass through a portion of the body of patient 14. As such any received signal by either external device 30 or IMD 10 may be relatively weak. Therefore, a noise floor may be relatively low as any received noise may interfere with the received signal or the received signal may be weak due to limited energy available on IMD 10 and a relatively small antenna being used for communication with external device 30.

According to the techniques of this disclosure, a telemetry system may include telemetry circuitry configured to communicate with a first device and being located on a circuit board; a first bobbin, the first bobbin being located on a first side of the circuit board; a first coil, the first coil being wound on the first bobbin in a first direction; a second bobbin, the second bobbin being located on a second side of the circuit board; a second coil, the second coil being wound on a second bobbin in a second direction, the second direction being opposite the first direction; wherein an outer loop of the first coil and an outer loop of the second coil are electrically coupled together.

According to the techniques of this disclosure, a telemetry system may include telemetry circuitry configured to communicate with a first device and being located on a circuit board; at least one bobbin, the at least one bobbin being located on a first side of the circuit board; a first coil, the first coil being wound on the at least one bobbin in a first direction; a second coil, the second coil being wound on the at least one bobbin in a second direction, the second direction being opposite the first direction; wherein an outer loop of the first coil and an outer loop of the second coil are electrically coupled together.

Figure 2:
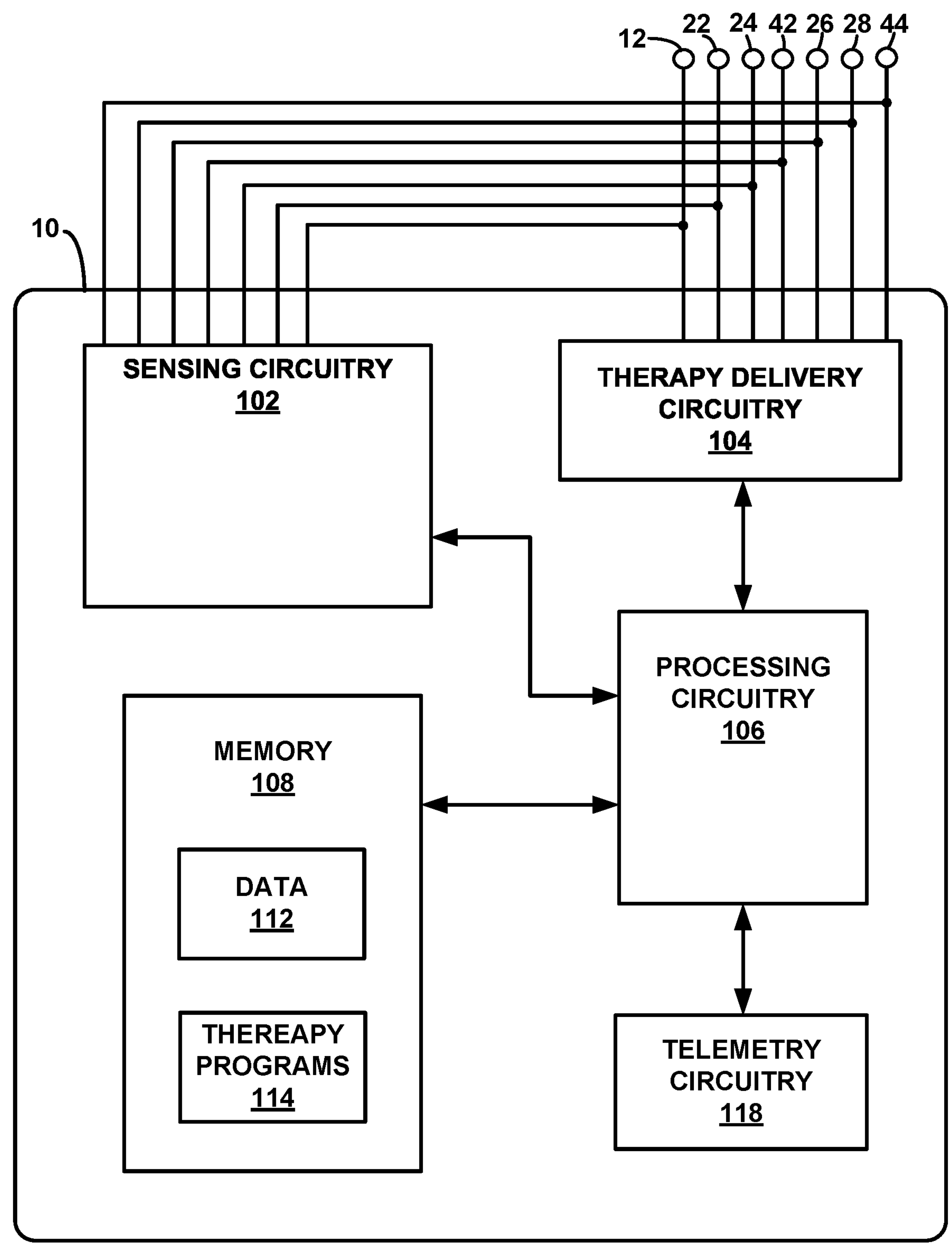
FIG. 2 is a functional block diagram of an example implantable medical device.

FIG. 2 is a functional block diagram of an example IMD. In the example illustrated by FIG. 2, IMD 10 includes sensing circuitry 102, therapy delivery circuitry 104, processing circuitry 106, associated memory 108, and telemetry circuitry 118. Processing circuitry 106 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 108 may store program instructions, which may include one or more program modules, which are executable by processing circuitry 106. When executed by processing circuitry 106, such program instructions may cause processing circuitry 106 and IMD 10 to provide the functionality ascribed to them herein. The program instructions may be embodied in software, firmware and/or RAMware. Memory 108 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 102 is configured to receive cardiac electrical signals from selected combinations of two or more of electrodes 22, 24, 26, 28, 42 and 44 carried by the ventricular lead 20 and atrial lead 21, along with housing electrode 12. Sensing circuitry 102 is configured to sense cardiac events attendant to the depolarization of myocardial tissue, e.g., P-waves and R-waves. Sensing circuitry 102 may include switching circuitry for selectively coupling electrodes 12, 22, 24, 26, 28, 42, 44 to sensing circuitry 102 in order to monitor electrical activity of heart 16. In other examples, not shown in FIG. 2, sensing circuitry 102 may receive cardiac electrical signals from other electrodes such as one or more LV electrodes, as described above in relation to FIG. 1. The switching circuitry may include a switch array, switch matrix, multiplexer, or any other type of switching device suitable to selectively couple one or more of the electrodes to sensing circuitry 102. In some examples, processing circuitry 106 selects the electrodes to function as sense electrodes, or the sensing vector, via the switching circuitry within sensing circuitry 102.

Sensing circuitry 102 may include multiple sensing channels, each of which may be selectively coupled to respective combinations of electrodes 12, 22, 24, 26, 28, 42, 44 to detect electrical activity of a particular chamber of heart 16, e.g., an atrial sensing channel and one or more ventricular sensing channels. Each sensing channel may be configured to amplify, filter, and rectify the cardiac electrical signal received from selected electrodes coupled to the respective sensing channel to detect cardiac events, e.g., P-waves and/or R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

Sensing circuitry 102 outputs an indication to processing circuitry 106 in response to sensing of a cardiac event, in the respective chamber of heart 16 (e.g., detected P-waves or R-waves). In this manner, processing circuitry 106 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular or atrial fibrillation episodes. Sensing circuitry 102 may also pass one or more digitized EGM signals to processing circuitry 106 for analysis, e.g., for use in cardiac rhythm discrimination. Sensed and/or processed signals, or representations thereof, may be stored in data 112 of memory 108.

Processing circuitry 106 may control therapy delivery circuitry 104 to deliver electrical therapy, e.g., cardiac pacing, anti-tachyarrhythmia therapy, or cardioversion or defibrillation shock pulses, to heart 16 according to therapy parameters stored in therapy programs 114 of memory 108. Therapy delivery circuitry 104 is electrically coupled to electrodes 12, 22, 24, 26, 28, 42, 44, and is configured to generate and deliver electrical therapy to heart 16 via selected combinations of electrodes 12, 22, 24, 26, 28, 42, 44. Therapy delivery circuitry 104 may include charging circuitry, one or more charge storage devices, such as one or more high voltage capacitors and/or one or more low voltage capacitors, and switching circuitry that controls when the capacitor(s) are discharged to selected combinations of electrodes 12, 22, 24, 26, 28, 42, 44. Charging of capacitors to a programmed pulse amplitude and discharging of the capacitors for a programmed pulse width may be performed by therapy delivery circuitry 104 according to control signals received from processing circuitry 106.

Therapy programs 114 may store intervals, counters, or other data used by processing circuitry 106 to control the delivery of pacing pulses by therapy delivery circuitry 104. Such data may include intervals and counters used by processing circuitry 106 to control the delivery of pacing pulses to heart 16. The intervals and/or counters are, in some examples, used by processing circuitry 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing circuitry 102 are identified in part based on their occurrence outside a blanking interval and inside or outside of a refractory sensing interval. Events that occur within predetermined interval ranges are counted for detecting cardiac rhythms.

Telemetry circuitry 118 is used to communicate with external device 30, for transmitting data accumulated by IMD 10 and for receiving interrogation and programming commands from external device 30. For example, telemetry circuitry 118 may be used to transmit data 112 to external device 30 and/or receive therapy programs 114 from external device 30.

Figure 3:
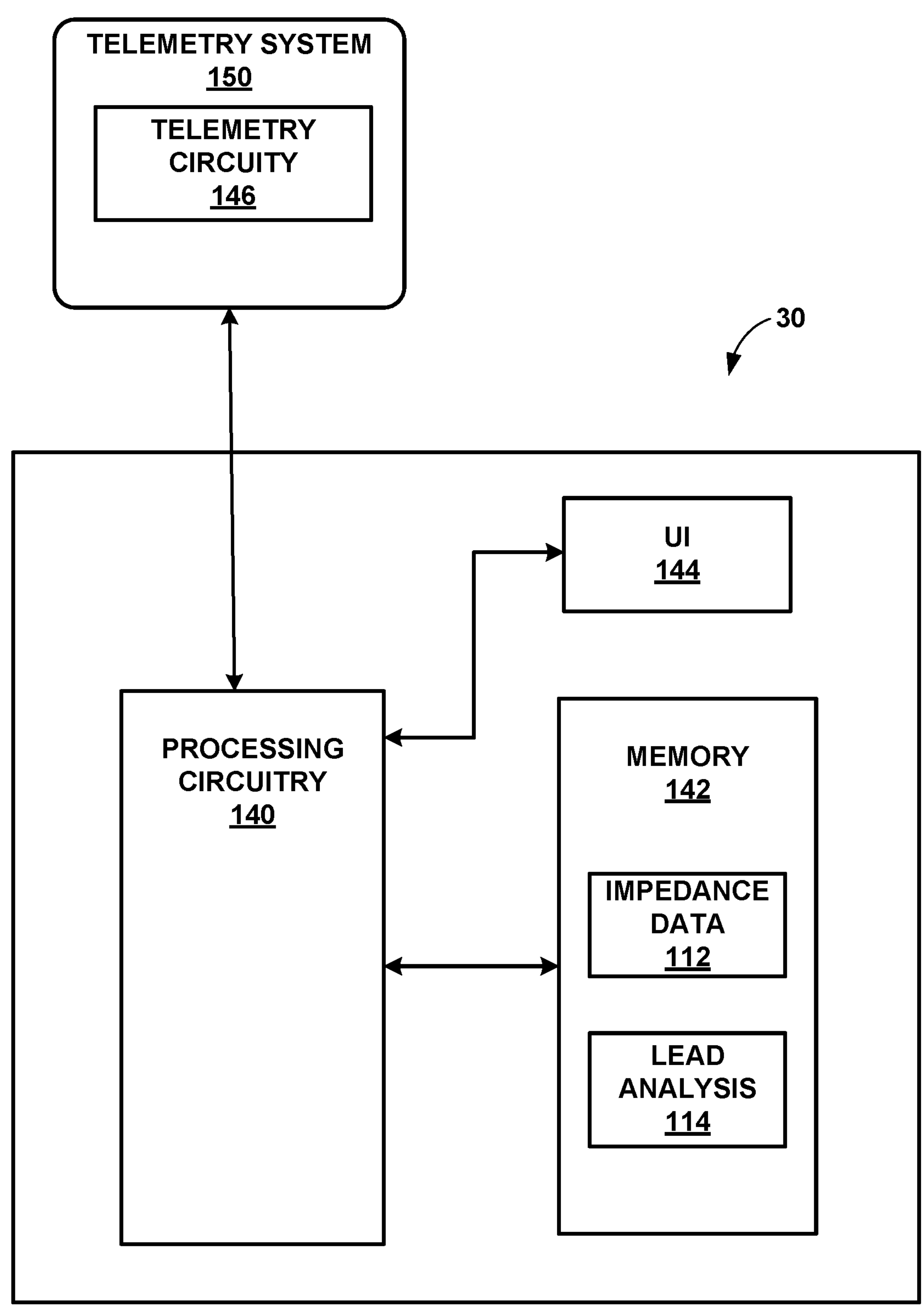
FIG. 3 is a functional block diagram of an example external device.

FIG. 3 is a functional block diagram of an example external device. In the example of FIG. 3, external device 30 includes processing circuitry 140, memory 142, and user interface (UI) 144. In some examples, external device includes telemetry circuitry 146. In other examples, as shown, external device 30 is electrically coupled to telemetry system 150 which may include telemetry circuitry 146.

For example, telemetry system 150 may include a programming head used with external device 30 to communicate with IMD 10. The programming head may include dual coils. For example, one coil may be located on one side of a circuit board including telemetry circuitry 146 and the other coil may be located on a different side of the circuit board or both coils may be located on a same side of the circuit board. Telemetry and/or noise signals may be induced on both coils. For example, telemetry signals from 1 MB 10 may be induced on both coils, but the coil that is closer to 1 MB 10 may receive a stronger induced signal voltage. By winding such coils in opposite directions and electrically coupling the outer loop of each coil together, a same induced signal on both would be canceled out. As far field magnetic field noise may be virtually the same voltage on both coils, far field magnetic field noise may be effectively rejected or reduced. Because a received telemetry signal may induce a stronger voltage on the closer coil, the received telemetry signal would not be effectively rejected. Electric field noise may tend to couple to the outer turns of each coil, so by electrically coupling the outer loop of each coil together the differential component of electric field noise can be shorted out. By shorting this connection to ground, the common mode electric field noise can be shorted out as well.

External device 30 may be a dedicated hardware device with dedicated software for the programming and/or interrogation of IMD 10. Alternatively, external device 30 may be an off-the-shelf computing device, e.g., running an application that enables external device 30 to program and/or interrogate IMD 10.

In some examples, a user uses external device 30 to select or program values for operational parameters of IMD 10, e.g., for cardiac sensing, therapy delivery, and lead integrity evaluation. In some examples, a user uses external device 30 to receive data 112 collected by IMD 10, such as physiological data of the patient or other operational and performance data of IMD 10. The user may interact with external device 30 via UI 144, which may include a display to present a graphical user interface to a user, and a keypad, touchpad or another mechanism for receiving input from a user. External device 30 may communicate wirelessly with IMD 10 using telemetry circuitry 146, which may be configured for wireless communication with telemetry circuitry 118 of IMD 10.

Processing circuitry 140 may include any combination of integrated circuitry, discrete logic circuitry, analog circuitry, such as one or more microprocessors, DSPs, ASICs, or FPGAs. In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 142 may store program instructions, which may include one or more program modules, which are executable by processing circuitry 140. When executed by processing circuitry 140, such program instructions may cause processing circuitry 140 and external device 30 to provide the functionality ascribed to them herein. The program instructions may be embodied in software and/or firmware. Memory 142 may include any volatile, non-volatile, magnetic, optical, or electrical media, such as a RAM, ROM, NVRAM, EEPROM, flash memory, or any other digital media.

Figure 4:
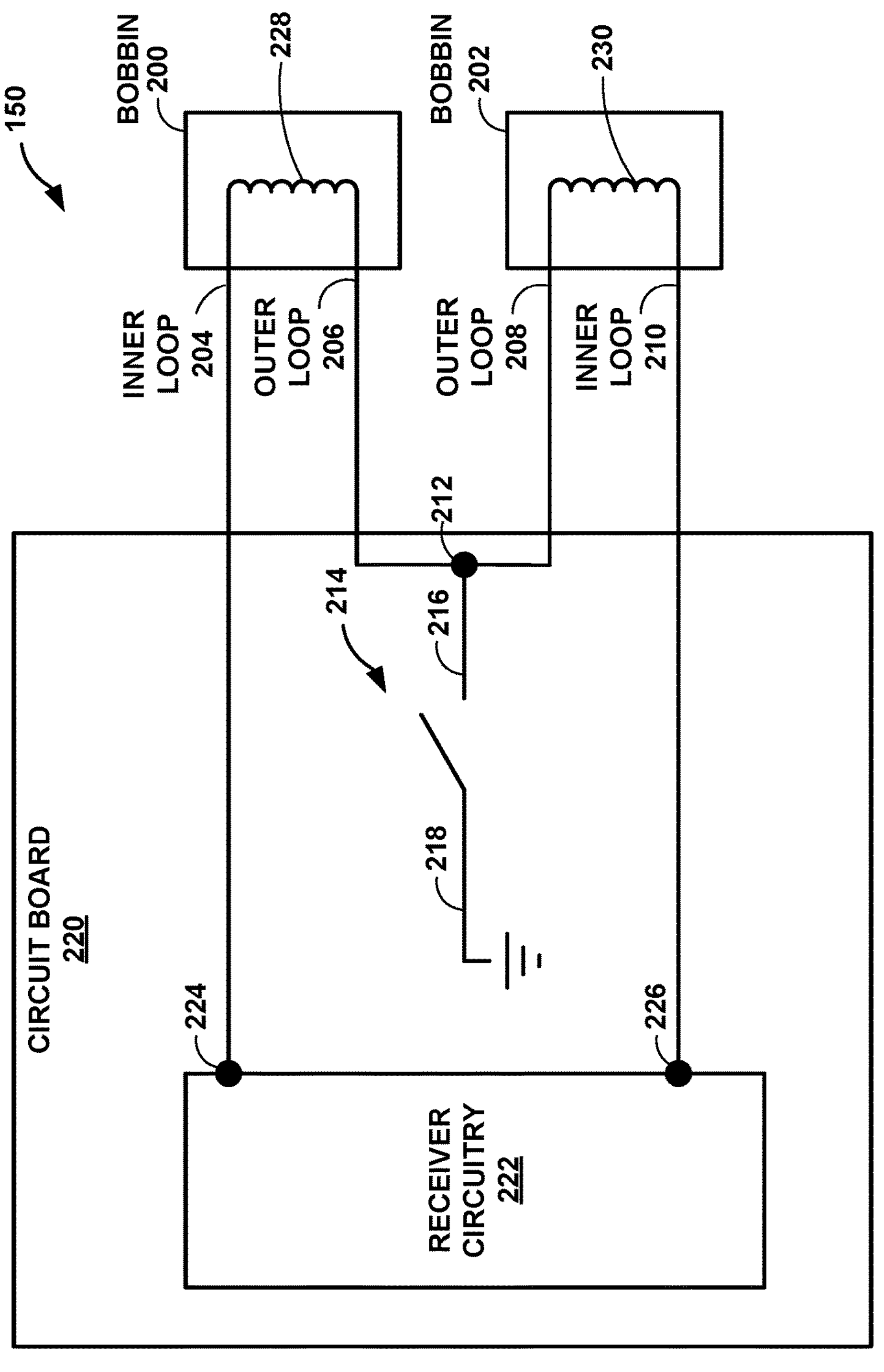
FIG. 4 is a conceptual diagram of an example telemetry system according to the techniques of this disclosure.

FIG. 4 is a conceptual diagram of an example telemetry system according to the techniques of this disclosure. Telemetry system 150 may include first bobbin 200, second bobbin 202, and circuit board 220. First bobbin 200 may be configured to hold first coil 228. First coil 228 may include an inner loop 204 and an outer loop 206. Second bobbin 202 may be configured to hold second coil 230. Second coil 230 may include an inner loop 210 and an outer loop 208. Outer loop 206 of first coil 228 may be electrically coupled to outer loop 208 of second coil 230. For example, both outer loop 206 and outer loop 208 may be electrically coupled to pin 212 of circuit board 220 or electrically coupled in circuit board 220, such that first coil 228 and second coil 230 are connected in series. First coil 228 may be wound in an opposite direction from second coil 230. By winding first coil 228 in an opposite direction from second coil 230 and electrically coupling outer loop 206 to outer loop 208, first coil 228 and second coil 230 may reject or reduce far field magnetic noise received across first coil 228 and second coil 230, as the far field noise will be effectively cancelled out. The directions of the winding are discussed in further detail with respect to FIG. 5 hereinafter. By winding the coils such that the outer loops are connected together, the differential mode electric field noise can be shorted out.

In some examples, first bobbin 200 is located on one side of circuit board 220 and second bobbin 202 is located on a different side of circuit board 220. In some examples, first bobbin 200 and second bobbin 202 are located on a same side of circuit board 220. In some examples, first bobbin 200 and second bobbin 202 are a same bobbin (not shown). For example, a single bobbin may hold both first coil 228 and second coil 230.

Inner loop 204 of first coil 228 may be electrically coupled to a first input 224 of receiver circuitry 222. Receiver circuitry 222 may be configured to receive telemetry signals captured by first coil 228 and second coil 230, for example, from IMD 10 (FIGS. 1-2). In some examples, receiver circuitry 222 includes a differential receiver. In some examples, receiver circuitry 222 also includes transmitter circuitry for enabling telemetry system 150 to transmit telemetry signals via first coil 228 and second coil 230 to, for example, IMD 10. In some examples, receiver circuitry 222 includes a differential receiver.

Optionally, telemetry system 150 may include switch 214. Switch 214 may include first portion 216 and second portion 218 for electrically coupling switch 214 to other components. First portion 216 of switch 214 may be electrically coupled to outer loop 206 of first coil 228 and to outer loop 208 of second coil 230, for example, through pin 212. Second portion of switch 214 may be electrically coupled to ground. Switch 214 may be configured to be open when telemetry system 150 is not actively receiving data and to be closed when telemetry system 150 is actively receiving data. For example, processing circuitry 140 (FIG. 3) of external device 30 may be configured to open and close switch 214. Alternatively, processing circuitry (not shown) of telemetry system 150 may be configured to open and close switch 214. In other examples, rather than including switch 214, pin 212 may be electrically coupled to ground, such as via a wire or a circuit board trace line (not shown). By electrically coupling pin 212 to ground at least when telemetry system 150 is actively transmitting or receiving data, addition rejection or reduction in common mode electric field noise may be achieved.

Figure 5:
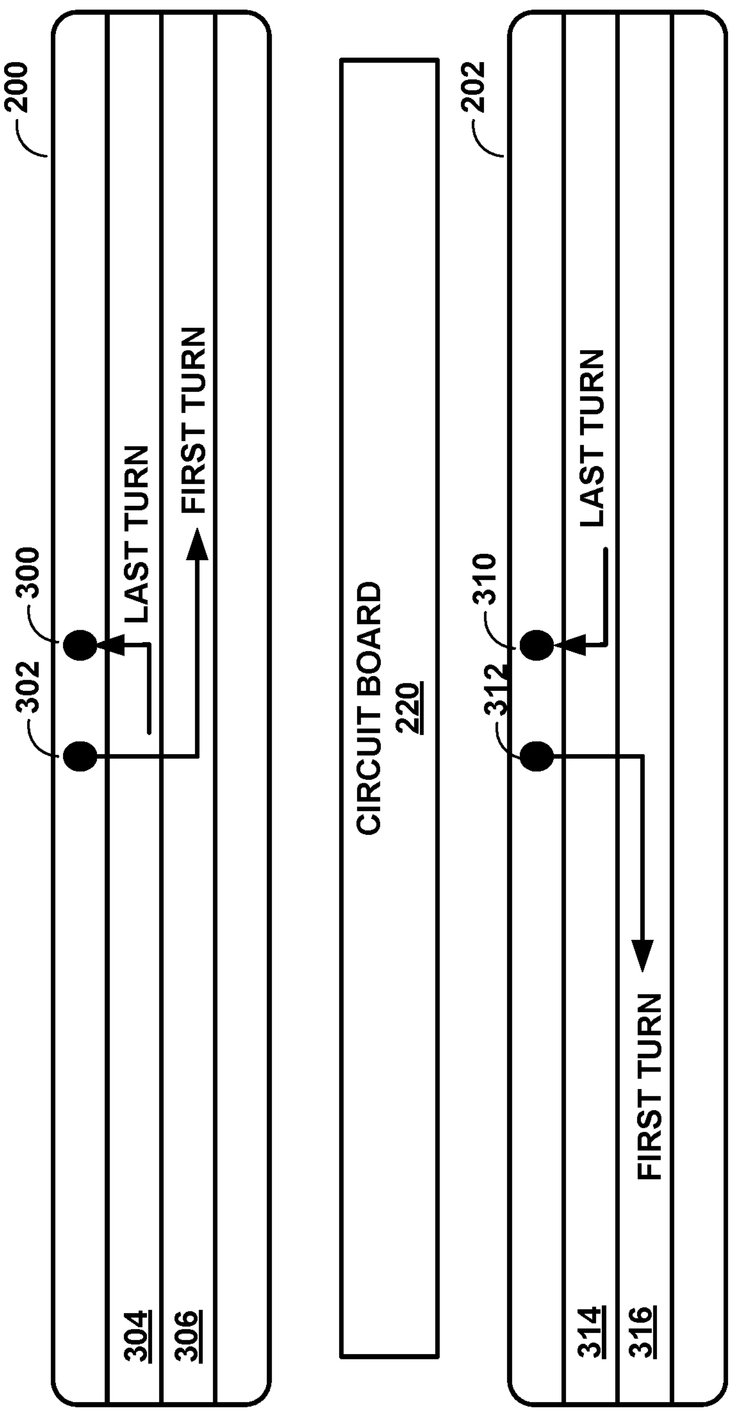
FIG. 5 is a conceptual diagram illustrating an example of the direction of loop of coils in the bobbins of a telemetry system.

FIG. 5 is a conceptual diagram illustrating an example of the direction of loop of coils in the bobbins of a telemetry system. First bobbin 200 is shown having groove 304 and groove 306 for holding first coil 228 (FIG. 4). While first bobbin 200 is shown having two grooves, first bobbin 200 may have any number of grooves, including no grooves at all. The first turn of first coil 228 is shown to be to the right in groove 306 from pin 302. The last turn of first coil 228 is from the left in groove 304 to pin 300.

Second bobbin 202 is shown having groove 314 and groove 316 for holding second coil 230 (FIG. 4). While second bobbin 202 is shown having two grooves, second bobbin 202 may have any number of grooves, including no grooves at all. The first turn of second coil 230 is shown to be to the left in groove 316 from pin 312. The last turn of second coil 230 is from the right in groove 314 to pin 310. In this manner, first coil 228 and second coil 230 are wound in opposite directions from each other around first bobbin 200 and second bobbin 202, respectively. In some examples, pin 300 and pin 310 are a same pin. In some examples, pin 300 and pin 310 are the same pin and are an example of pin 212 (FIG. 4). The grooves in which the turns of first coil 228 and second coil 230 are placed are provided merely as examples, and other placements of the turns of first coil 228 and second coil 230 are contemplated and still fall within the scope of this disclosure. Bobbins as described herein, e.g., first bobbin 200 and second bobbin 202, may have, but do not necessarily have, a cylindrical shape.

Absent the techniques of this disclosure, an electric field may induce a voltage on first coil 228 and second coil 300 in micro volts. In some examples, the voltage may be on the order of 2-4 micro volts even with the use capacitive electric field shield covers. Such a voltage may be on the order of 10 times larger than noise floor. However, by winding the first coil 228 and second coil 230 in opposite directions and electrically coupling the outer loops together, far field electric field noise may be effectively shorted or canceled out.

Figure 6:
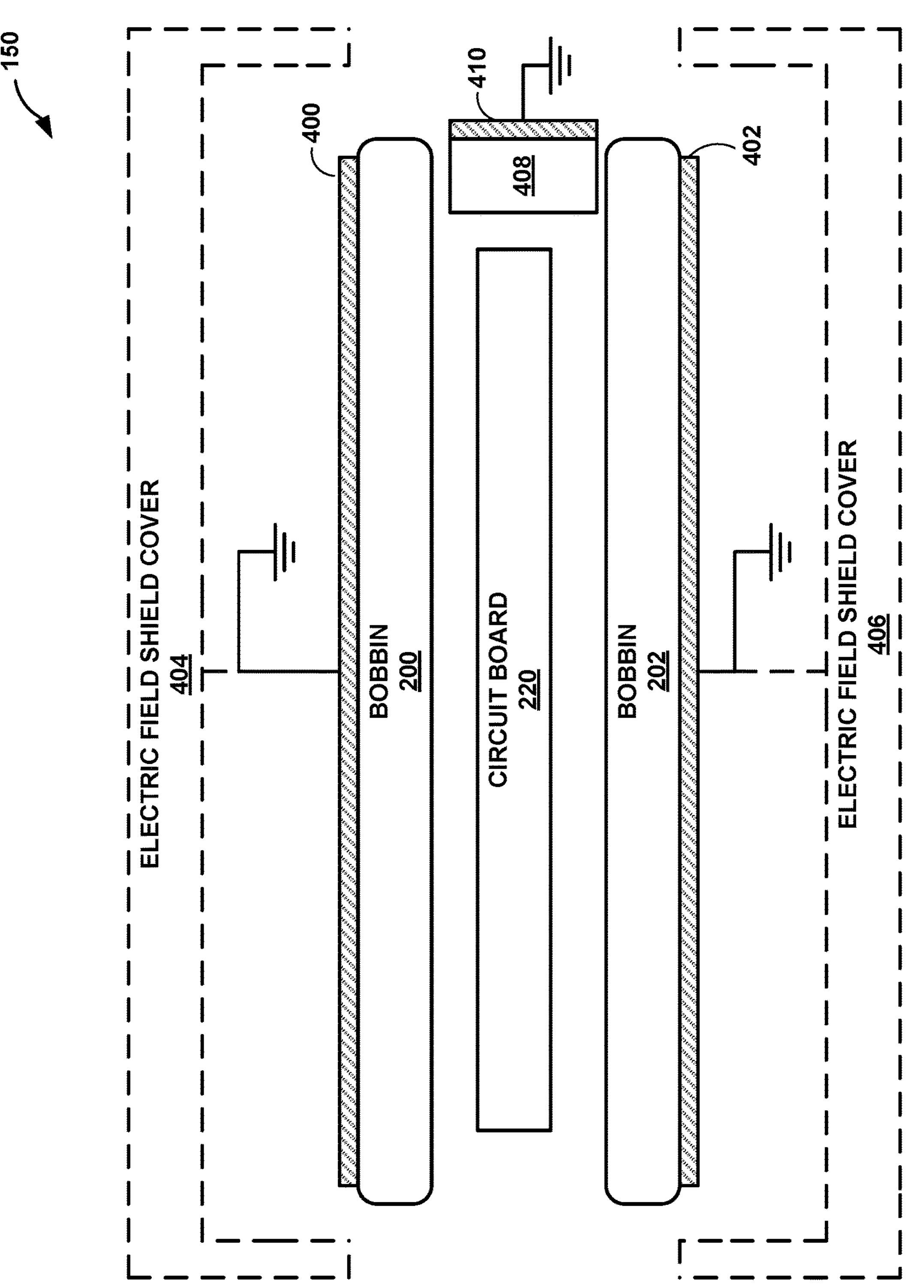
FIG. 6 is a block diagram of an exploded view of an example telemetry system according to the techniques of this disclosure.

FIG. 6 is a block diagram of an exploded view of an example telemetry system according to the techniques of this disclosure. Telemetry system 150 may include a programming head. The programming head may include first bobbin 200 located on one side (e.g., a top side) of circuit board 220 and second bobbin 202 located on another side (e.g., a bottom side) of circuit board 220. First bobbin 200 may include a first conductive coating 400, such as a spray conductive coating which may be sprayed on to a surface of first bobbin 200, such as an outer surface facing away from circuit board 220. In some examples, the outer surface, the inner surface, or both of first bobbin 200 may include first conductive coating 400. Second bobbin 202 may similarly include a second conductive coating 402, such as a spray conductive coating which may be sprayed on to a surface of second bobbin 202, such as an outer surface facing away from circuit board 220. In some examples, the outer surface, the inner surface, or both of second bobbin 202 may include second conductive coating 402. First conductive coating 400 and second conductive coating 402 may be electrically coupled to ground. In some examples, first conductive coating 400 and second conductive coating 402 may be electrically coupled to ground outside of circuit board 220. In some examples, first conductive coating 400 and second conductive coating 402 may be electrically coupled to ground on circuit board 220.

Optionally, telemetry system may include one or more electric field shield cover, such as electric field shield cover 404 or electric field shield cover 406. The one or more electric field shield covers may be configured to reject or reduce additional electric field noise. In some examples, the one or more electric field shield covers may substantially surround first bobbin 200, circuit board 220, and second bobbin 202. For example, the one or more electric field shield covers may cover a majority of the outer surfaces (surfaces not facing circuit board 220) of first bobbin 200 and second bobbin 202, which in turn may cover the majority of the surfaces of circuit board 220. In some examples, the one or more electric field shield covers may also be coupled to ground. In this manner, the one or more electric field shield covers may better reject or reduce additional electric field noise reaching first coil 228 and second coil 230 (FIG. 4).

In some examples, the one or more electric field shield covers may form a housing for telemetry system 150. In other examples, first bobbin 200 and second bobbin 202 may form a housing for telemetry system 150. In yet another example, telemetry system 150 may include a different housing (not shown).

In some examples, one or more interconnect pads or gaskets, such as interconnect pad 408 may be located between first bobbin 200 and second bobbin 202. In some examples, the one or more interconnect pads or gaskets may separate first bobbin 200 from second bobbin 202 such that circuit board 220 is not damaged by first bobbin 200 or second bobbin 202. In some examples, the one or more interconnect pads or gaskets may be made of foam. In some examples, the one or more interconnect pads or gaskets may include a third conductive coating 410, such as first conductive coating 400 or second conductive coating 402. In some examples, third conductive coating 410 of the one or more interconnect pads may be electrically coupled to ground.

In some examples, telemetry system 150 includes telemetry circuitry 146 (FIG. 3) configured to communicate with a first device and being located on circuit board 220. In some examples, telemetry system 150 includes first bobbin 200, first bobbin 200 being located on a first side (e.g., top side) of circuit board 220. In some examples, telemetry system 150 include first coil 228, first coil 228 being wound on first bobbin 200 in a first direction. In some examples, telemetry system 150 includes second bobbin 202, second bobbin 202 being located on a second side (e.g., bottom side) of circuit board 220. In some examples, telemetry system 150 includes second coil 230, second coil 230 being wound on second bobbin 202 in a second direction, the second direction being opposite the first direction. In some examples, outer loop 206 of first coil 228 and outer loop 208 of second coil 230 are electrically coupled together. In some examples, outer loop 206 of first coil 228 and outer loop 208 of second coil 230 are electrically coupled together by being coupled to a same pin 212 or in circuit board 220.

In some examples, telemetry circuitry 146 includes differential receiver (e.g., receiver circuitry 222), the differential receiver including first receiver input 224 and second receiver input 226, inner loop 204 of first coil 228 being electrically coupled to first receiver input 224 and inner loop 210 of second coil 230 being electrically coupled to second receiver input 226. In some examples, telemetry system 150 includes switch 214 configured to be open when the receiver of telemetry system 150 is not in use and to be closed when the receiver of telemetry system 150 is in use. In some examples, first portion 216 of switch 214 is electrically coupled to outer loop 206 of first coil 228 and outer loop 208 of second coil 230, and second portion 218 of switch 214 is electrically coupled to ground 240.

In some examples, a first conductive coating 400 is located on a surface of first bobbin 200 and a second conductive coating 402 is located on a surface of second bobbin 202. In some examples, first conductive coating 400 and second conductive coating 402 are electrically coupled to ground.

In some examples, telemetry system 150 further includes at least one shield cover (e.g., electric field shield cover 404 and/or electric field shield cover 406). In some examples, the at least one shield cover substantially surrounds first bobbin 200 and second bobbin 202. In some examples, first bobbin 200 comprises a first plastic structure and second bobbin 202 comprises a second plastic structure. In some examples, first bobbin 200 and second bobbin 202 comprise a single plastic structure.

In some examples, the device is an 1 MB and telemetry circuitry 146 is configured to receive data from the 1 MB via first coil 228 and second coil 230. In some examples, telemetry system 150 includes a computing device (e.g., external device 30 of FIGS. 1, 3) comprising processing circuitry (e.g., processing circuitry 140 of FIG. 3), the processing circuitry being configured to process the received data.

Figure 7:
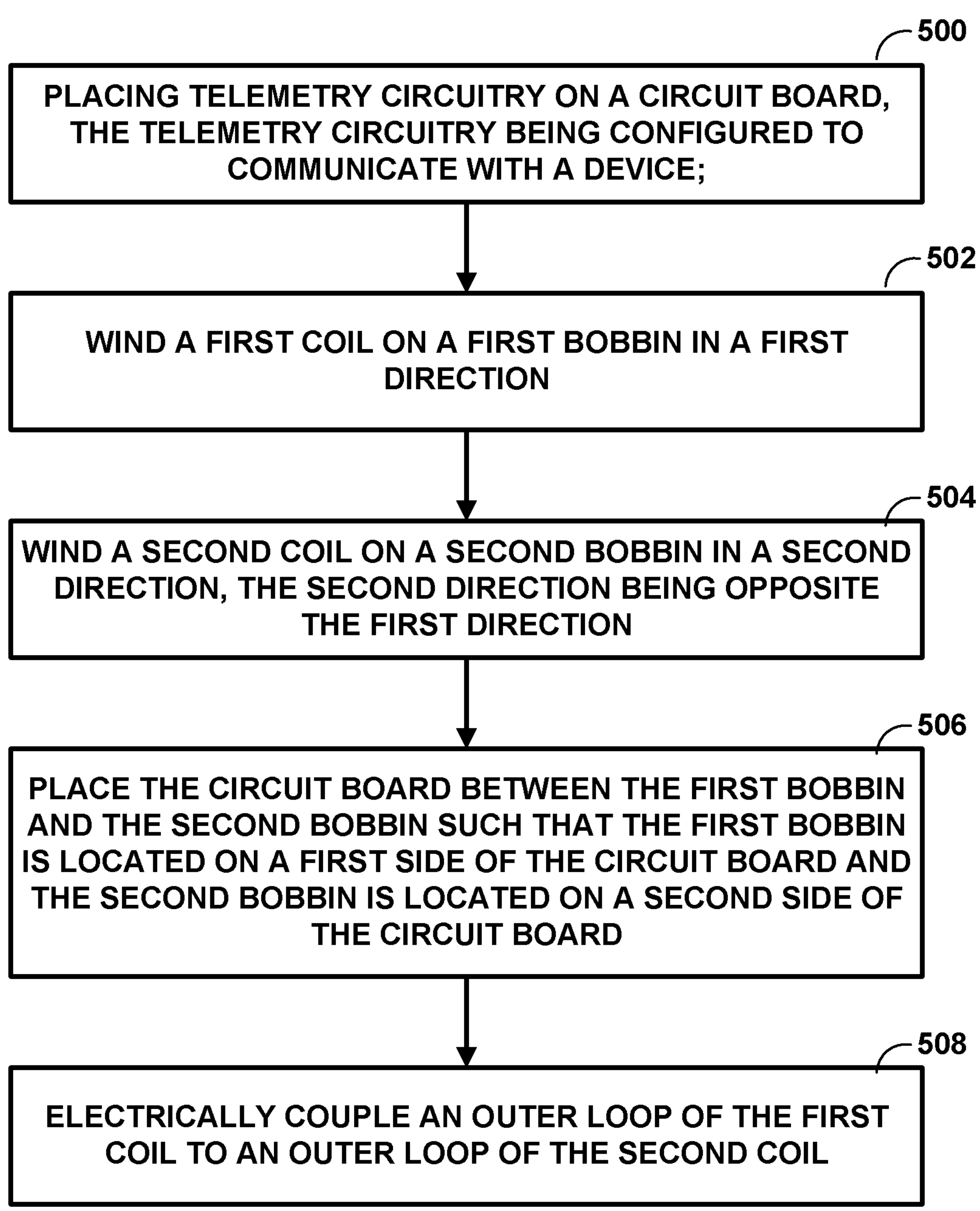
FIG. 7 is a flow diagram illustrating example manufacturing techniques for a telemetry system.

FIG. 7 is a flow diagram illustrating example manufacturing techniques for a telemetry system. A manufacturer may place telemetry circuitry 146 on circuit board 220, the telemetry circuitry being configured to communicate with a device (500). For example, a machine or person may fabricate telemetry circuitry 146 on circuit board 220 or otherwise integrate telemetry circuitry 146 onto circuit board 220. A manufacturer may wind first coil 228 on first bobbin 200 in a first direction (502). For example, a machine or person may wind first coil 228 on first bobbin 200 with inner loop 204 going toward the right and outer loop 206 coming from the left. A manufacturer may wind second coil 230 on second bobbin 202 in a second direction, the second direction being opposite the first direction (504). For example, a machine or person may wind second coil 230 on second bobbin 202 with inner loop 208 going toward the left and outer loop 210 coming from the right.

A manufacturer may place circuit board 220 between first bobbin 200 and second bobbin 202 such that first bobbin 200 is located on a first side of circuit board 220 and second bobbin 202 is located on a second side of circuit board 220 (506). For example, a machine or person may move circuit board 220, first bobbin 200, and/or second bobbin 202 such that circuit board 220 is located between first bobbin 200 and second bobbin 202. A manufacturer may electrically couple outer loop 206 of first coil 228 to outer loop 208 of second coil 230. For example, a machine or person may electrically couple outer loop 206 of first coil 228 and outer loop 208 of second coil 230 to a same pin 212, or the coupling may occur on or within circuit board 220.

In some examples, telemetry circuitry 146 includes a differential receiver (e.g., receiver circuitry 222), the differential receiver including first receiver input 224 and second receiver input 226. In some examples, a manufacturer may electrically couple inner loop 204 of first coil 228 to first receiver input 224 and electrically couple inner loop 210 of second coil 230 to second receiver input 226. In some examples, a manufacturer may electrically couple first portion 216 of switch 214 to outer loop 206 of first coil 228 and outer loop 208 of second coil 230. In some examples, a manufacturer may electrically couple second portion 218 of switch 214 to ground. In some examples, the switch is configured to be open when telemetry system 150 is not actively receiving data and to be closed when telemetry system 150 is actively receiving data.

In some examples, a manufacturer may deposit first conductive coating 400 on a surface of first bobbin 200. In some examples, a manufacturer may deposit second conductive coating 402 on a surface of second bobbin 402. In some examples, a manufacturer may electrically couple first conductive coating 400 and second conductive coating 402 to ground.

In some examples, a manufacturer may place at least one shield cover (e.g., electric field shield cover 404 or electric field shield cover 406) to substantially surrounding first bobbin 200 and second bobbin 202. In some examples, first bobbin 200 includes a first plastic structure and second bobbin 202 includes a second plastic structure. In some examples, first bobbin 200 and second bobbin 202 include a single plastic structure.

In some examples, telemetry circuitry 146 is configured to, during operation, receive data from IMD 10 via first coil 228 and second coil 230. In some examples, a manufacturer or person may electrically couple telemetry system 150 to a computing device (e.g., external device 30), the computing device including processing circuitry (e.g., processing circuitry 140), the processing circuitry being configured to process the received data during operation of the computing device.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

This disclosure contains the following non-limiting examples.

Example 1. A telemetry system comprising: telemetry circuitry configured to communicate with a first device and being located on a circuit board; a first bobbin, the first bobbin being located on a first side of the circuit board; a first coil, the first coil being wound on the first bobbin in a first direction; a second bobbin, the second bobbin being located on a second side of the circuit board; and a second coil, the second coil being wound on the second bobbin in a second direction, the second direction being opposite the first direction; wherein an outer loop of the first coil and an outer loop of the second coil are electrically coupled together.

Example 2. The telemetry system of example 1, wherein the outer loop of the first coil and the outer loop of the second coil are electrically coupled together by being coupled to a same pin or by being coupled in the circuit board.

Example 3. The telemetry system of example 1 or 2, wherein the telemetry circuitry comprises a differential receiver, the differential receiver comprising a first receiver input and a second receiver input, an inner loop of the first coil being electrically coupled to the first receiver input and an inner loop of the second coil being electrically coupled to the second receiver input.

Example 4. The telemetry system of any of examples 1-3, further comprising a switch configured to be open when the telemetry system receiver is not in use and to be closed when the telemetry system receiver is in use, wherein a first portion of the switch is electrically coupled to the outer loop of the first coil and the outer loop of the second coil, and a second portion of the switch is electrically coupled to ground.

Example 5. The telemetry system of any of examples 1-4, further comprising: a first conductive spray coating located on a surface of the first bobbin; and a second conductive spray coating located on a surface of the second bobbin, wherein the first conductive spray coating and the second conductive spray coating are electrically coupled to ground.

Example 6. The telemetry system of any of examples 1-5, further comprising: at least one shield cover, the at least one shield cover substantially surrounding the first bobbin and the second bobbin.

Example 7. The telemetry system of any of examples 1-6, wherein the first bobbin comprises a first plastic structure and the second bobbin comprises a second plastic structure.

Example 8. The telemetry system of any of examples 1-6, wherein the first bobbin and the second bobbin comprise a single plastic structure.

Example 9. The telemetry system of any of examples 1-8, wherein the first device is an implantable medical device and wherein the telemetry circuitry is configured to receive data from the implantable medical device via the first coil and the second coil.

Example 10. The telemetry system of example 9, further comprising a computing device comprising processing circuitry, the processing circuitry being configured to process the received data.

Example 11. A method comprising: placing telemetry circuitry on a circuit board, the telemetry circuitry being configured to communicate with a device; winding a first coil on a first bobbin in a first direction; winding a second coil on a second bobbin in a second direction, the second direction being opposite the first direction; placing the circuit board between the first bobbin and the second bobbin such that the first bobbin is located on a first side of the circuit board and the second bobbin is located on a second side of the circuit board; and electrically coupling an outer loop of the first coil to an outer loop of the second coil.

Example 12. The method of example 11, wherein electrically coupling the outer loop of the first coil to the outer loop of the second coil comprises electrically coupling the outer loop of the first coil and the outer loop of the second coil to a same pin or in the circuit board.

Example 13. The method of example 11 or 12, wherein the telemetry circuitry comprises a differential receiver, the differential receiver comprising a first receiver input and a second receiver input, and wherein the method further comprises: electrically coupling an inner loop of the first coil to the first receiver input; and electrically coupling an inner loop of the second coil to the second receiver input.

Example 14. The method of any of examples 11-13, further comprising: electrically coupling a first portion of a switch to the outer loop of the first coil and the outer loop of the second coil; and electrically coupling a second portion of the switch to ground, wherein the switch is configured, during operation of a computing device, to be open when a telemetry system is not in use and to be closed when the telemetry system is in use.

Example 15. The method of any of examples 11-14, further comprising: depositing a first conductive spray coating on a surface of the first bobbin; depositing a second conductive spray coating on a surface of the second bobbin; and electrically coupling the first conductive spray coating and the second conductive spray coating to ground.

Example 16. The method of any of examples 11-15, further comprising: placing at least one shield cover to substantially surrounding the first bobbin and the second bobbin.

Example 17. The method of any of examples 11-16, wherein the first bobbin comprises a first plastic structure and the second bobbin comprises a second plastic structure.

Example 18. The method of example 17, wherein the first plastic structure and the second plastic structure comprise a single plastic structure.

Example 19. The method of any of examples 11-18, wherein the telemetry circuitry is configured to, during operation, receive data from an implantable medical device via the first coil and the second coil.

Example 20. The method of example 19, further comprising: electrically coupling the telemetry circuitry to a computing device comprising processing circuitry, the processing circuitry being configured to process the received data during operation of the computing device.

Example 21. A telemetry system comprising: telemetry circuitry configured to communicate with a first device and being located on a circuit board; at least one bobbin, the at least one bobbin being located on a first side of the circuit board; a first coil, the first coil being wound on the at least one bobbin in a first direction; a second coil, the second coil being wound on the at least one bobbin in a second direction, the second direction being opposite the first direction; wherein an outer loop of the first coil and an outer loop of the second coil are electrically coupled together.

Various examples have been described. These and other examples are within the scope of the following claims.

What is claimed is:

1. A telemetry system for communicating with an implantable medical device, the telemetry system comprising:

telemetry circuitry configured to wirelessly communicate with the implantable medical device and being located on a circuit board;

a first bobbin, the first bobbin being located on a first side of the circuit board;

a first coil, the first coil being wound on the first bobbin in a first direction;

a second bobbin, the second bobbin being located on a second side of the circuit board; and a second coil, the second coil being wound on the second bobbin in a second direction, the second direction being opposite to the first direction;

wherein an outer loop of the first coil and an outer loop of the second coil are electrically coupled together; and a switch configured to be open when a telemetry system receiver is not in use and to be closed when the telemetry system receiver is in use, wherein a first portion of the switch is electrically coupled to the outer loop of the first coil and the outer loop of the second coil, and a second portion of the switch is electrically coupled to ground.

2. The telemetry system of claim 1, wherein the outer loop of the first coil and the outer loop of the second coil are electrically coupled together by being coupled to a same pin or by being coupled in the circuit board.

3. The telemetry system of claim 1, wherein the telemetry circuitry comprises a differential receiver, the differential receiver comprising a first receiver input and a second receiver input, an inner loop of the first coil being electrically coupled to the first receiver input and an inner loop of the second coil being electrically coupled to the second receiver input.

4. The telemetry system of claim 1, further comprising:

a first conductive spray coating located on a surface of the first bobbin; and a second conductive spray coating located on a surface of the second bobbin, wherein the first conductive spray coating and the second conductive spray coating are electrically coupled to the ground.

5. The telemetry system of claim 1, further comprising:

at least one shield cover, the at least one shield cover substantially surrounding the first bobbin and the second bobbin.

6. The telemetry system of claim 1, wherein the first bobbin comprises a first plastic structure and the second bobbin comprises a second plastic structure.

7. The telemetry system of claim 1, wherein the first bobbin and the second bobbin comprise a single plastic structure.

8. The telemetry system of claim 1, wherein a first device is the implantable medical device and wherein the telemetry circuitry is configured to receive data from the implantable medical device via the first coil and the second coil.

9. The telemetry system of claim 8, further comprising a computing device comprising processing circuitry, the processing circuitry being configured to process the received data.

10. A method comprising:

placing telemetry circuitry on a circuit board, the telemetry circuitry being configured to wirelessly communicate with an implantable medical device;

winding a first coil on a first bobbin in a first direction;

winding a second coil on a second bobbin in a second direction, the second direction being opposite to the first direction;

placing the circuit board between the first bobbin and the second bobbin such that the first bobbin is located on a first side of the circuit board and the second bobbin is located on a second side of the circuit board; and electrically coupling an outer loop of the first coil to an outer loop of the second coil; and a switch configured to be open when a telemetry system receiver is not in use and to be closed when the telemetry system receiver is in use, wherein a first portion of the switch is electrically coupled to the outer loop of the first coil and the outer loop of the second coil, and a second portion of the switch is electrically coupled to ground.

11. The method of claim 10, wherein electrically coupling the outer loop of the first coil to the outer loop of the second coil comprises electrically coupling the outer loop of the first coil and the outer loop of the second coil to a same pin or in the circuit board.

12. The method of claim 10, wherein the telemetry circuitry comprises a differential receiver, the differential receiver comprising a first receiver input and a second receiver input, and wherein the method further comprises:

electrically coupling an inner loop of the first coil to the first receiver input; and electrically coupling an inner loop of the second coil to the second receiver input.

13. The method of claim 10, further comprising:

electrically coupling first portion of the switch to the outer loop of the first coil and the outer loop of the second coil; and electrically coupling a second portion of the switch to the ground, wherein the switch is configured, during operation of a computing device, to be open when a telemetry system is not in use and to be closed when the telemetry system is in use.

14. The method of claim 10, further comprising:

depositing a first conductive spray coating on a surface of the first bobbin;

depositing a second conductive spray coating on a surface of the second bobbin; and electrically coupling the first conductive spray coating and the second conductive spray coating to the ground.

15. The method of claim 10, further comprising:

placing at least one shield cover to substantially surrounding the first bobbin and the second bobbin.

16. The method of claim 10, wherein the first bobbin comprises a first plastic structure and the second bobbin comprises a second plastic structure.

17. The method of claim 16, wherein the first plastic structure and the second plastic structure comprise a single plastic structure.

18. The method of claim 10, wherein the telemetry circuitry is configured to, during operation, wirelessly receive data from the implantable medical device via the first coil and the second coil.

19. A telemetry system for communicating with an implantable medical device, the telemetry system comprising:

telemetry circuitry configured to wirelessly communicate with a first the implantable medical device and being located on a circuit board;

at least one bobbin, the at least one bobbin being located on a first side of the circuit board;

a first coil, the first coil being wound on the at least one bobbin in a first direction;

a second coil, the second coil being wound on the at least one bobbin in a second direction, the second direction being opposite to the first direction, wherein an outer loop of the first coil and an outer loop of the second coil are electrically coupled together; and a switch configured to be open when a telemetry system receiver is not in use and to be closed when the telemetry system receiver is in use, wherein a first portion of the switch is electrically coupled to the outer loop of the first coil and the outer loop of the second coil, and a second portion of the switch is electrically coupled to ground.

* * * * *